US007820964B2

(12) United States Patent
Beecher

(10) Patent No.: US 7,820,964 B2
(45) Date of Patent: Oct. 26, 2010

(54) METHOD FOR GENERATION AND USE OF STABLE ISOTOPE PATTERNS IN MASS SPECTRAL DATA

(75) Inventor: Christopher William Ward Beecher, Ann Arbor, MI (US)

(73) Assignee: Metabolic Analyses, Inc, Chapel Hill, NC (US)

( * ) Notice: Subject to any disclaimer, the term of this patent is extended or adjusted under 35 U.S.C. 154(b) by 151 days.

(21) Appl. No.: 12/186,395

(22) Filed: Aug. 5, 2008

(65) Prior Publication Data

US 2009/0039247 A1 Feb. 12, 2009

Related U.S. Application Data

(60) Provisional application No. 60/654,253, filed on Aug. 6, 2007, provisional application No. 60/976,923, filed on Oct. 2, 2007.

(51) Int. Cl.
*B01D 59/44* (2006.01)
*H01J 49/00* (2006.01)

(52) U.S. Cl. ................ 250/282; 250/281; 250/288; 506/12; 204/228.7

(58) Field of Classification Search ................ 250/282, 250/281, 288; 506/12; 204/228.7
See application file for complete search history.

(56) References Cited

U.S. PATENT DOCUMENTS

| 6,790,673 | B1 | 9/2004 | Kingston |
| 6,849,396 | B2 | 2/2005 | Schneider |
| 6,940,065 | B2 | 9/2005 | Graber et al. |
| 6,952,818 | B2 | 10/2005 | Schneider et al. |
| 7,045,296 | B2 | 5/2006 | Parker et al. |
| 2004/0195500 | A1 | 10/2004 | Sachs et al. |
| 2005/0069916 | A1* | 3/2005 | Chait et al. ............ 435/6 |
| 2007/0176088 | A1 | 8/2007 | Li |
| 2007/0195500 | A1 | 8/2007 | Cheng et al. |
| 2009/0039246 | A1* | 2/2009 | Beecher ............ 250/282 |
| 2009/0124518 | A1* | 5/2009 | Beecher ............ 506/22 |

FOREIGN PATENT DOCUMENTS

| WO | WO 2009/021056 | 2/2009 |
| WO | WO 2009/021059 | 2/2009 |
| WO | WO 2009/046204 | 4/2009 |

OTHER PUBLICATIONS

WO 2009/021056 International Search Report.

(Continued)

*Primary Examiner*—Nikita Wells
(74) *Attorney, Agent, or Firm*—Husch Blackwell Welsh & Katz

(57) ABSTRACT

A composition adapted for mass spectral analysis is disclosed as are methods of its use in mass spectral analyses. A contemplated composition contains a mass spectrally-determinable amount of each of (i) at least one analyte to be assayed and (ii) a standard compound. Each of the molecules of the standard compound contains one or the other of a pair of two stable isotopes of the same element that differ in molecular weight by at least two atomic mass units. Those two isotopes are present in the molecules of the standard compound in a predetermined ratio that is other than the naturally occurring ratio of those isotopes.

21 Claims, 4 Drawing Sheets

OTHER PUBLICATIONS

WO 2009/046204 International Search Report.
WO 2009/021059 International Search Report.
Hellerstein, *Metabolic Engineering* 6:85-100 (2004).
Williams et al., *Experimantal Cell Research* 69:106-112 (1971).
Wu et al., *Anal Biochem* 336:164-171 (2005).
Katajamaa et al., BMC *Bioinformatics* 2005, 6:179 doi:10.1186/1471-2105-6-179.
Rögnvaldsson et al., 2004 *J. Chrom. B*, 807:209-215; doi:10.1016/j.jchromb.2004.04.010.
Johannsen, 1911 *American Naturalist* 45:129-159.

* cited by examiner

1/1 RATIO

2/1 RATIO

Fig. 2.C
3/1 RATIO
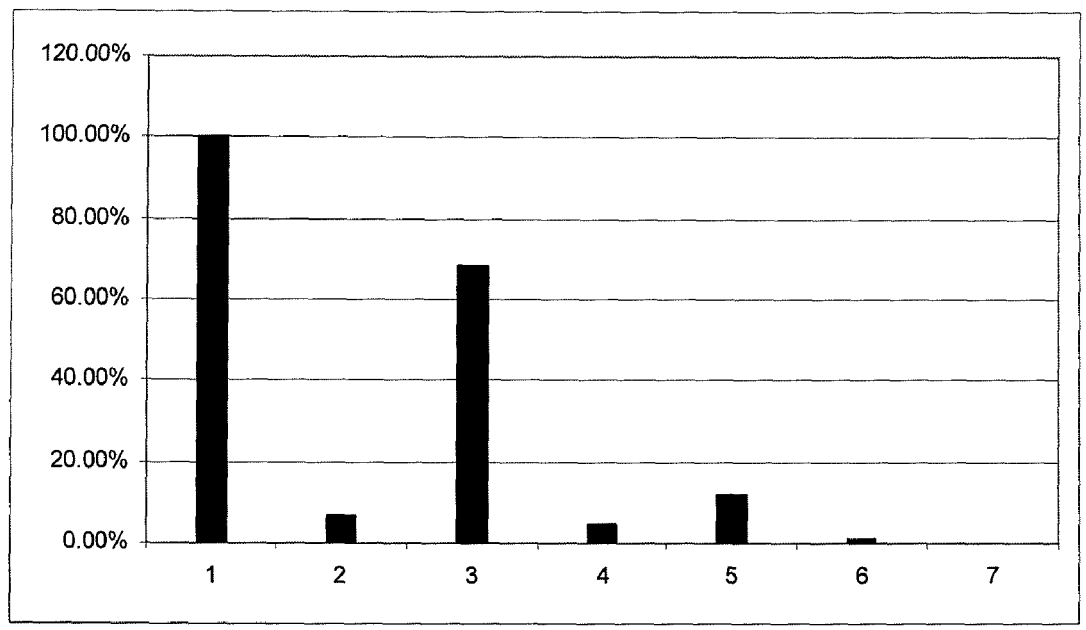
Fig. 2D
1/2 RATIO
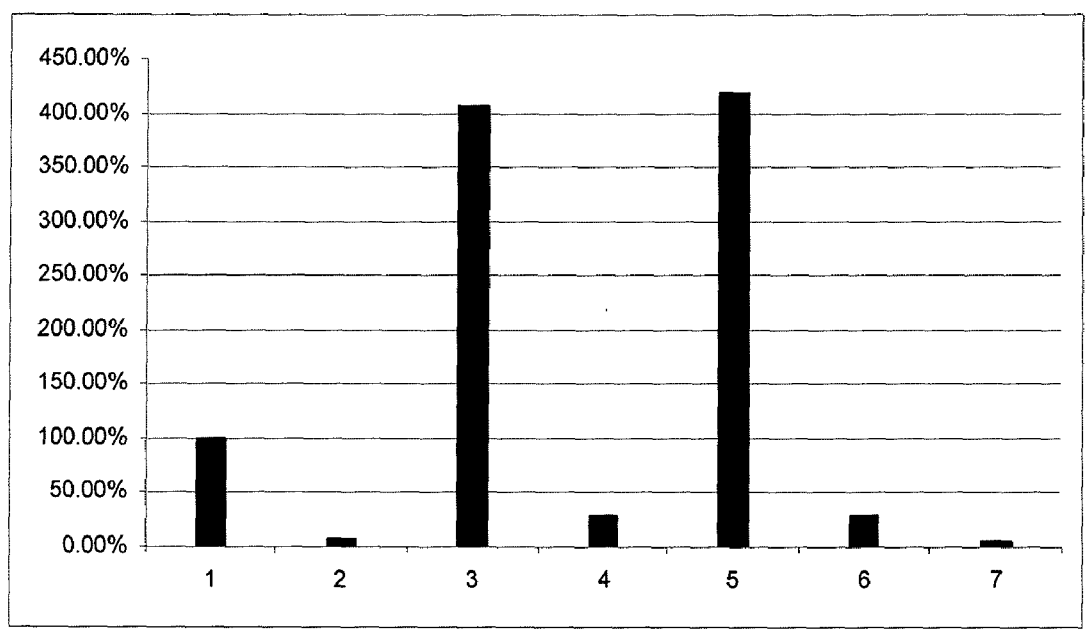

US 7,820,964 B2

METHOD FOR GENERATION AND USE OF STABLE ISOTOPE PATTERNS IN MASS SPECTRAL DATA

CROSS-REFERENCE TO RELATED APPLICATION

This application claims benefit of Provisional Patent application No. 60/954,253, entitled "A method for the production and use of mass spectral standards" filed on Aug. 6, 2007, and Provisional Patent application No. 60/976,923 entitled "Method for the generation and use of isotopic patterns in mass spectral data" filed on Oct. 2, 2007, which are hereby incorporated by reference.

TECHNICAL FIELD

The present application relates to the creation and use of stable isotope patterns in the mass spectral analyses. These patterns can be introduced through either biological or non-biological methods, or combinations of both. More specifically, a contemplated method utilizes a compound with a predefined and unique stable isotope pattern as a standard. The isotopic ratios are not altered by a biological system.

BACKGROUND ART

The use of stable isotopes for the determination of biological information has a long and illustrious history [see, Hellerstein, *Metabolic Engineering* 6:85-100 (2004)]. The oldest and most frequent such usage is in studies probing metabolism wherein a stable isotope is incorporated into a specific molecule at a specific location. This isotopically-labeled molecule, or "precursor", is fed to an in vivo organism, in vitro cell system, or in vitro cell-free system for either a brief or extended period of time, after which the fate of the isotope is determined, either by use of NMR, mass spectrometry (MS), chemical degradation, or other detection technique.

In contrast to the use of radioactive isotopes, the use of stable isotopes is generally regarded as safe and free of regulation. Although in general, a study typically uses a single isotope incorporated into a specific location in order to achieve a precision in understanding the metabolic fate of a molecule, another embodiment of the use of stable isotopes utilizes wholly-labeled molecules (>99% of an atom is replaced with an isotopic equivalent), or universally-labeled (the isotope is universally distributed within the target molecule at less than saturation levels). There are many known studies in which more than one isotope is incorporated into a target molecule, and all of the isotopic fragments are examined for their differential fates. In all cases, these methods are targeted analyses; i. e., they seek the incorporation of a specific labeled atom into other specific molecules.

Yet another use of stable isotopically labeled compounds is as internal standards for their non-labeled counterparts. In such a use, an isotopically enriched molecule is added to a sample or extract at a known concentration prior to an analysis, and the final measurement determines the exact concentration of the non-labeled material by comparison. In this type of study, it is not uncommon for a researcher to add more than one isotopically-distinct standard if more than one molecule is to be quantified.

Indeed, there are extreme forms where one prepares an extremely complex mixture by growing a complex organism on an isotopically-defined feedstock such that the entire organism is heavily, if not entirely, composed of molecules consisting of only one isotope [Wu et al., *Anal Biochem* 336:164-171 (2005)]. In this situation, the same standard is introduced into all samples, but there is no information carried by the standard other than for purposes of relative quantitation; i. e., the standard has no relation to the experiment at hand. Historically, such standards are carefully constructed to differ from any other analyte by a specific mass difference.

In many areas of science the need for reproducible chromatographic separations is fundamental. However, the most common approach is to repeatedly test the equipment prior to running the sample to be analyzed, because the inherent variability of chromatographic systems is an unfortunate and unsolvable problem. There are solutions to this problem in which compounds not native to the injected sample are added or "spiked" at predetermined concentrations before injection, and used as reference points in the eluent stream. These compounds are referred to as chromatographic standards.

In all such cases, the time of elution (and possibly the quantitation) is/are then mathematically corrected according to the position (and size) of the standards peaks. When this is done then the chromatogram is based not on "retention time" but on "retention index". This strategy works well when the standards can be easily identified and are separated from the other constituents of the sample either in time or other physical characteristic, such as mass.

Unfortunately this is all too frequently not the case. If another compound co-elutes from the column in the vicinity of the standard and shares any common ions, then the standard is unusable. For this reason, the use of several such standards is frequently required in order to assure that one or more of the standards will be useable.

Ion suppression is a phenomenon that occurs during the mass spectroscopic ionization processes when the efficiency of sample ionization is subjected to variability due to characteristics of the analyte compounds that are present. Thus, in its most common form, the number of molecules that could be ionized is in excess of the amount of charge available. In this situation the molecules that become ionized most efficiently are those that can acquire the charge most strongly, and the remaining molecules become ionized with much lower efficiency.

The present invention provides a method for creation and use of patterns of stable isotope as internal standards in mass spectral analyses. Thus, a contemplated method utilizes a compound with a predefined, unique and non-natural ratio of stable isotopes as a standard and thereby provides one solution to mass spectral analysis problems associated with ion suppression as wells as providing a more general standard that can be used in assaying multiple types of systems.

BRIEF SUMMARY OF THE INVENTION

In one aspect, the invention contemplates a composition that is adapted for mass spectral analysis. The composition is comprised of a mass spectrally-determinable amount of each of (i) at least one analyte to be analyzed and (ii) a standard compound. The analyte can be any one or more molecules that is/are assayable by mass spectrum and thus has a molecular weight of less than about 5000 atomic mass units (amu), and preferably less than about 1000 amu. Each of the molecules of the standard compound contains one or the other of two stable isotopes of the same element that differ in molecular weight by at least two atomic mass units. Those two isotopes are present in a predetermined ratio that is other than the naturally occurring ratio of those isotopes. Due to the presence of these isotopes each compound acquires a unique molecular profile of two or more peaks that readily distinguishes it from any natural compound.

Another aspect of the invention contemplates a method for determining the correctness of a mass spectrographic assay of a sample. This method contemplates the steps of providing a sample for analysis that comprises a composition adapted for mass spectral analysis that contains a mass spectrally-determinable amount of each of (i) at least one analyte to be assayed and (ii) a standard compound. Each of the molecules of the standard compound contains one or the other of a pair of two stable isotopes of the same element that differ in molecular weight by at least two atomic mass units. More than one pair of such isotopes can also be used. The two isotopes are present in the molecules of the standard compound in a predetermined ratio that is other than the naturally occurring ratio of those isotopes. The mass spectral analysis of the sample is carried out to provide a set of analyte ion peaks, including peaks for the ions produced by the standard compound molecules that contain the two isotopes.

The ratio of the two peaks to each other is determined. That determined peak ratio is compared to the predetermined ratio of the peaks present in the molecules of the standard compound prior to the mass spectral analysis. A determined isotopic ratio that is within experimental error of the predetermined ratio indicates that the results of the mass spectral analysis were correct and serve to identify the "standard", whereas a determined isotopic ratio that is greater than experimental error of the predetermined ratio indicates that the results of the mass spectral analysis include a contribution from an unanticipated source. In this case, the multiplicity of the information content derived from the "standard" permit one to remove the unanticipated contribution.

Another, similar method, can be used for determining the correctness of a chromatographic separation of a sample. In this method, a chromatographically separated sample for analysis is provided that comprises a composition adapted for mass spectral analysis that contains a mass spectrally-determinable amount of each of (i) at least one analyte to be assayed and (ii) a standard compound. Each of the molecules of the standard compound contains one or the other of a pair of two stable isotopes of the same element that differ in molecular weight by at least two atomic mass units. Again, more than one pair of such isotopes can also be used. The two isotopes are present in the molecules of the standard compound in a predetermined ratio that is other than the naturally occurring ratio of those isotopes.

The mass spectral analysis of the sample is carried out to provide a set of analyte ion peaks, including peaks for the ions produced by the standard compound molecules that contain the two isotopes. The ratio of the two isotopes to each other in the standard compound peaks is determined and then compared to the predetermined ratio of the isotopes present in the molecules of the standard compound prior to the mass spectral analysis. A determined isotopic ratio being within experimental error of the predetermined ratio indicates that the standard has been correctly found, whereas a determined isotopic ratio being greater or lesser than experimental error of the predetermined ratio indicates that the standard has been found but was contaminated by another component.

BRIEF DESCRIPTION OF THE DRAWINGS

In the drawings forming a portion of this disclosure,

FIG. 1 in four panels.

Figure 1A:
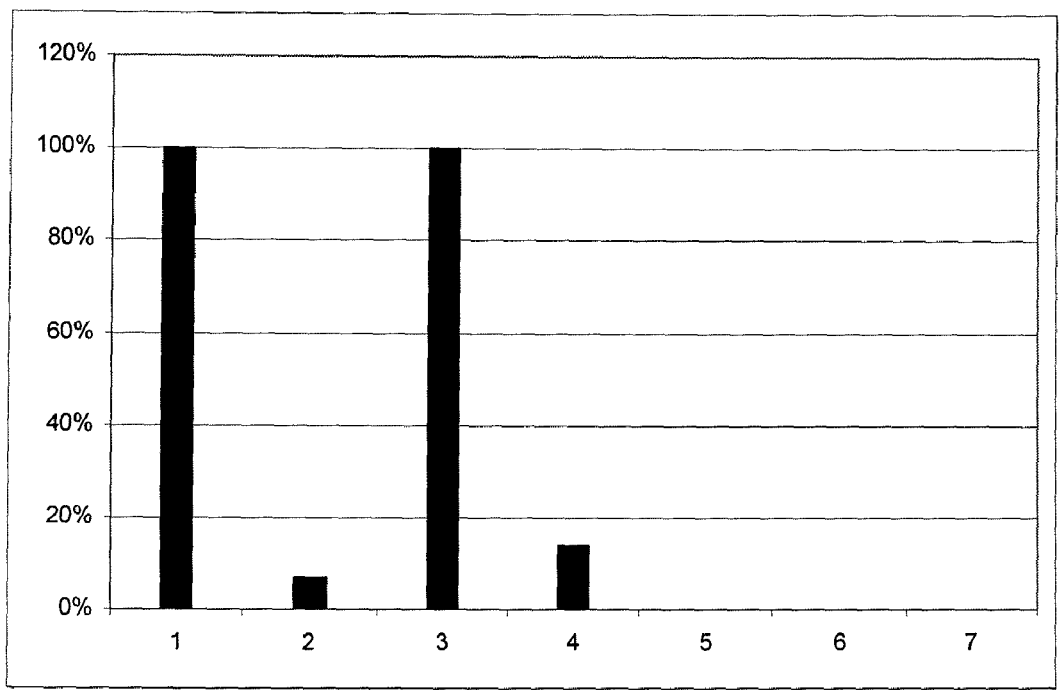
FIG. 1A-D, illustrates hypothetical mass spectra that show a variety of patterns that can be created by placing 1 (1A), 2 (1B), 3 (1C), or 4 (1D) chlorines into a $C_6H_{12}O_6$ sugar molecule in place of hydrogens, where the chlorine used in the synthesis has an initial ratio of Cl-35/Cl-37 (50:50).
Figure 1B:
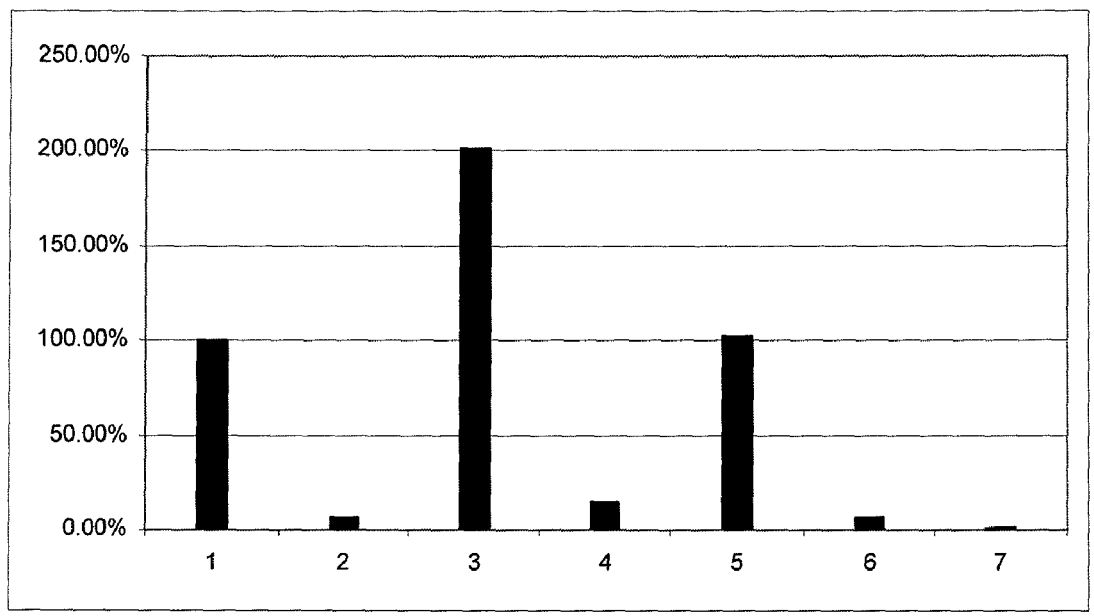
Figure 1C:
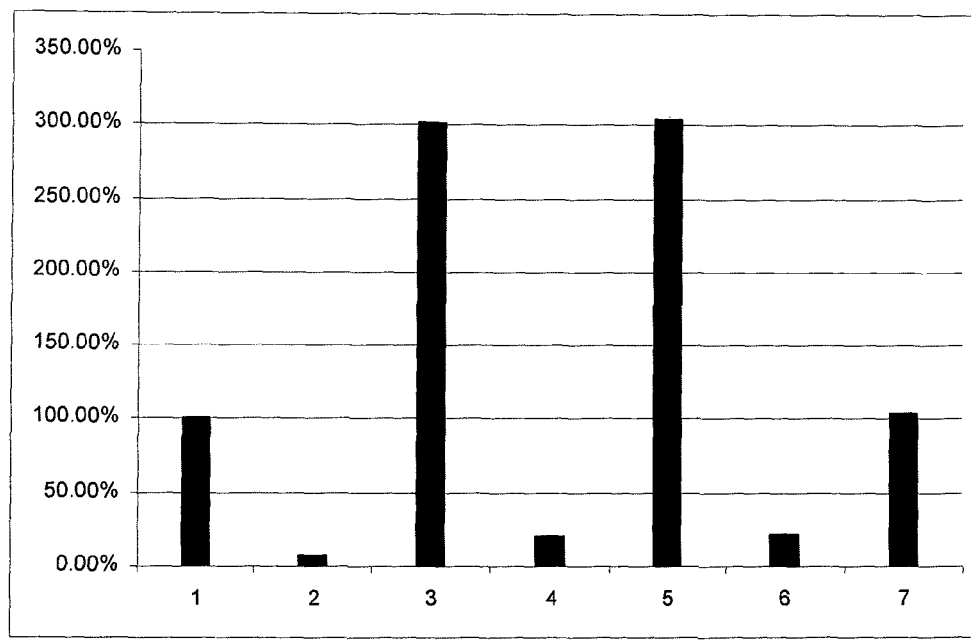
Figure 1D:
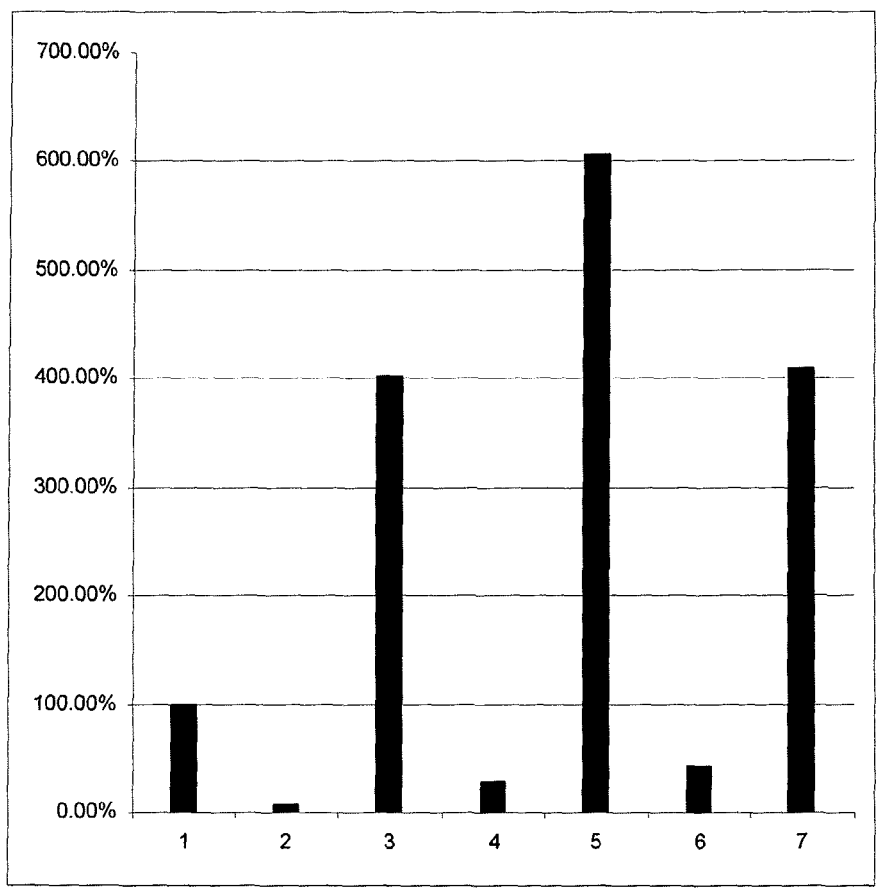

The present invention has several benefits and advantages.

One benefit is that by the use of specifically designed isotopic ratios one can identify the standard peak within the totality of analyte peaks seen in the spectrum, irrespective of spectral complexity. Specifically, any spectral signal can a) originate from the control culture, or b) experimental culture, or c) be an artifact acquired during sample preparation, or d) originate from the externally applied standard. Each of these classes of compounds has unique characteristics and isotopic signatures according to experimental design; however the standard has patterns not achievable by natural means.

One advantage of the invention is that variation that is experimentally introduced; i.e., "noise", can be statistically nullified and/or greatly minimized.

Another benefit of the invention is that at the liquid chromatography-mass-spectral interface, there is a loss of signal due to "ion suppression". Ion suppression occurs whenever there is more compound than charge availability. In this situation, some compounds become charged at the expense of other compounds. The variability of ionization efficiency is such that some molecules cannot be accurately quantified. The present method almost fully removes the problem of ion suppression because a compound's ability to ionize is a function of its structure and is not significantly altered by its isotopic distribution.

In a liquid chromatographic analysis there is some minor variation that can be corrected by the inclusion of a chromatographic standard for injection size, and alignment. Yet another benefit of the invention provides a means of this correction, so that sample to sample variation can be better understood.

In the processing of any biological sample for an analysis there is also some minor variation that can be understood as part of a Quality Assurance/Quality Control (QA/QC) program. In some cases the information derived from these variations is correctable or if not, the results must be disregarded. Another advantage of the invention is that it provides means by which this correction of sample to sample variation can be better understood.

Still further benefits and advantages of the invention will be apparent to the skilled worker from the disclosure that follows.

DETAILED DESCRIPTION OF THE INVENTION

In one aspect, the invention contemplates a composition that is adapted for mass spectral analysis. The composition is comprised of a mass spectrally-determinable amount of each of (i) at least one analyte to be analyzed and (ii) a standard compound. The analyte can be any one or more molecules that is/are assayable by mass spectrum and thus has a molecular weight of less than about 5000 atomic mass units (amu), and preferably less than about 1000 amu.

Each of the molecules of the standard compound contains one or the other of two stable isotopes of the same element that differ in molecular weight by at least two atomic mass units. Those two isotopes are present in a predetermined ratio that is other than the naturally occurring ratio of those isotopes. It is to be understood that more than one such pair can be present and that when more than one pair is present in a given standard molecule those atoms can be isotopes of the same or different elements. Thus, a single standard compound can have one pair of Cl-35 and Cl-37 in its molecules, or two or more such pairs. In addition, the standard can have one pair of Cl-35 and Cl-37 atoms and a pair of Br-79 and Br-81 atoms, and the like.

Another aspect of the invention contemplates a method for determining the correctness of a mass spectrographic assay of a sample. This method contemplates providing a sample for analysis that comprises a composition adapted for mass spectral analysis that contains a mass spectrally-determinable amount of each of (i) at least one analyte to be assayed and (ii) a standard compound. A composition discussed above is one such sample.

Each of the molecules of the standard compound contains one or the other of a pair of two stable isotopes of the same element that differ in molecular weight by at least two atomic mass units. More than one pair of such isotopes can also be used as discussed previously. The two isotopes are present in the molecules of the standard compound in a predetermined ratio that is other than the naturally occurring ratio of those isotopes. The isotopic ratio of the standard compound need only be different enough from the naturally occurring ratio that that ratio could not occur in nature. The mass spectral analysis of the sample is carried out to provide a set of analyte ion peaks, including peaks for the ions produced by the standard compound molecules that contain the two isotopes.

The ratio of the pair of two isotopes (or further pairs of isotopes as may be present) to each other is determined. That determined isotope ratio is compared to the predetermined ratio of the isotopes present in the molecules of the standard compound prior to the mass spectral analysis. A determined isotopic ratio that is within experimental error of the predetermined ratio indicates that the Standard is correctly found and uncontaminated, whereas a determined isotopic ratio that is greater or lesser than experimental error of the predetermined ratio indicates that the standard molecule is found but is contaminated by ions from another compound.

Figure 2A:
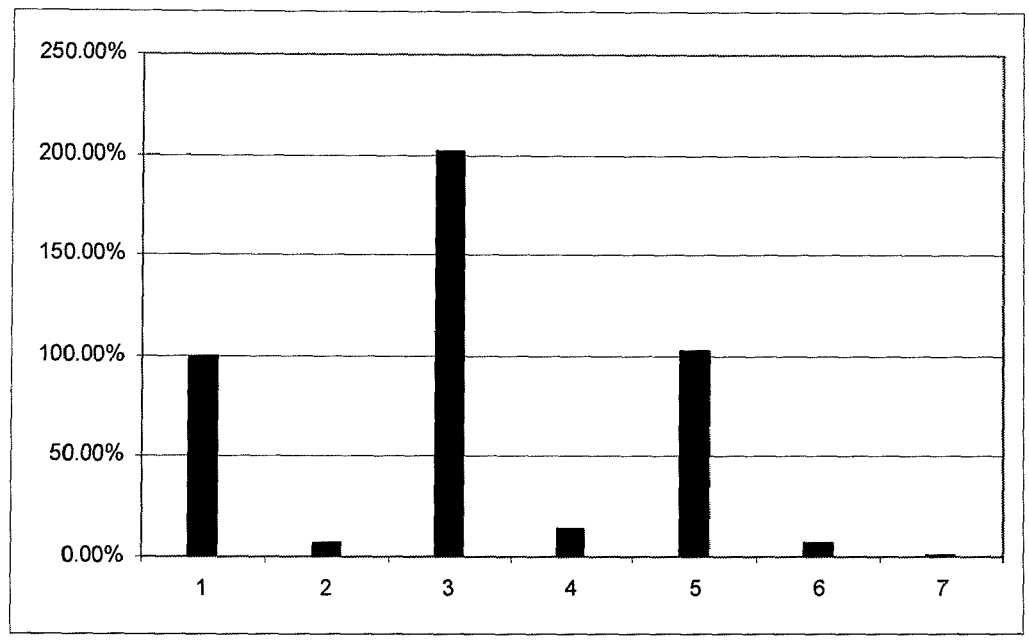
FIG. 2 in four panels, 2A-D, illustrates a hypothetical mass spectrum of a compound showing the "parent peak" at "1" on the abscissa and the variety of patterns that can be created by placing 2 chlorines into the molecule where the initial ratio of Cl-35/Cl-37 is varied at 1/1 (2A), 2/1 (2B), 3/1 (2C) and 1/2 (2D).
Figure 2B:
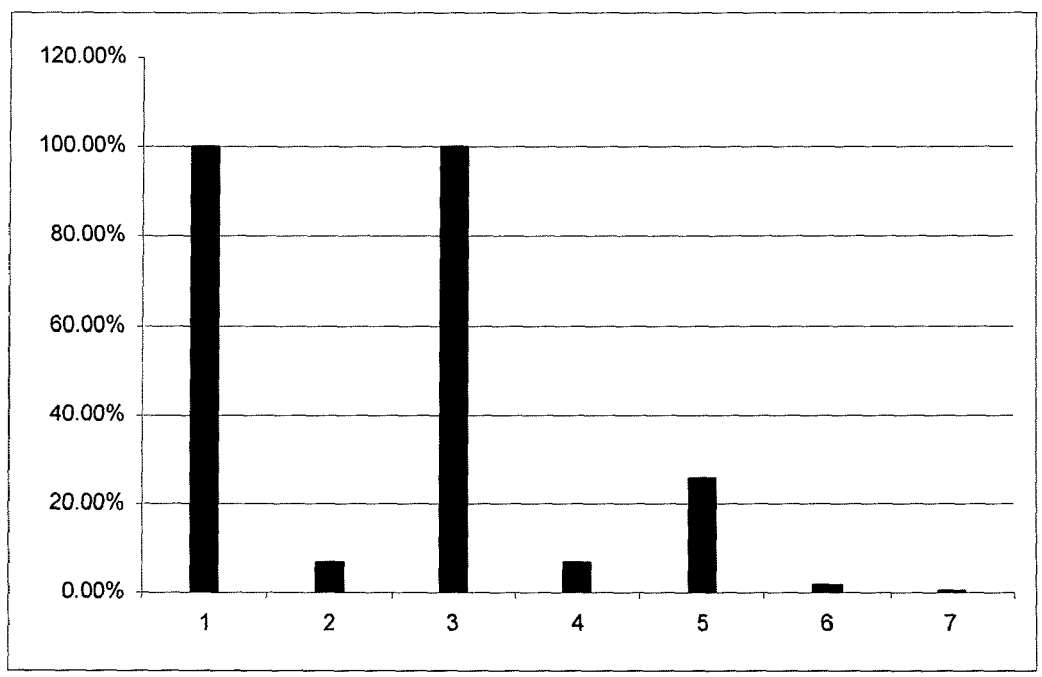

In one contemplated manifestation of this method, the standard compounds are introduced into a sample for mass spectral analysis, generally after biological treatment has ceased, with no assumption that they will be transformed, but rather with specific, predetermined and highly diagnostic isotopic ratios in their makeup such that they can be identified (see FIGS. 1 and 2) in the presence of other materials.

For example, a compound with a distinct non-naturally abundant isotopic profile can be admixed with a sample as an internal standard to determine its percent recovery, derivatization, injection, or other characteristic of a process. If the standard is synthesized to have a specific non-natural pattern in its isotopic makeup, it can be readily identified by mass spectroscopic analysis. In addition to ready identification of the standard, if one of the sought-after analyte isotopic peaks has been contaminated by a random compound, that fact is readily apparent because that analyte will have an unexpected ratio relative to the rest of the "normal" pattern. This situation is readily identifiable and quantification can be corrected for the presence of a contaminant.

In many areas of science the need for reproducible chromatographic separations is fundamental. However, the most common approach is to repeatedly test the equipment prior to running the sample to be analyzed, because the inherent variability of chromatographic systems is an unfortunate and unsolvable problem. There are solutions to this problem in which compounds not native to the injected sample are added or "spiked" at predetermined concentrations before injection, and used as reference points in the eluent stream. These compounds are referred to as chromatographic standards.

In such cases, the time of elution (and possibly the quantification) is mathematically corrected according to the position (and size) of the standards peaks. When this is done, the chromatogram is based not on "retention time" but on "retention index". This strategy works well when the standards can be easily identified and are separated from the other constituents of the sample either in time or other physical characteristic, such as mass. Unfortunately this is all too frequently not the case. If another compound co-elutes from the column in the vicinity of the standard and shares any common ions, then the standard is unusable. For this reason, the use of several such standards is frequently required in order to assure that one or more of the standards will be useable. Standards for use in chromatographic separations typically have molecular weights of about 500 to about 750 amu.

In the present method, analyte compounds to be used as a standard have two or more peaks when assayed in a mass spectrometer, and these peaks have carefully predetermined ratios. In this situation, because the pattern introduces a certain level of redundancy, any of the peaks carry all of the information, and therefore it is much less likely that a compound used as a standard would become useless due to contamination in a mass spectrometer. In addition, such standards are very easy to locate using automated systems or software that seeks them.

Thus, another aspect of this invention contemplates a method for determining the correctness of a chromatographic separation. Here, a chromatographically separated sample for analysis is provided that comprises a composition adapted for mass spectral analysis that contains a mass spectrally-determinable amount of each of (i) at least one analyte to be assayed and (ii) a standard compound. Each of the molecules of the standard compound contains one or the other of a pair of two stable isotopes of the same element that differ in molecular weight by at least two atomic mass units. Those two isotopes are present in the molecules of said standard compound in a predetermined ratio that is other than the naturally occurring ratio of those isotopes, as discussed previously.

A mass spectral analysis of the sample is carried out to provide a set of analyte ion peaks, including peaks for the ions produced by the standard compound molecules that contain said two isotopes. The ratio of the two isotopes to each other in the standard compound peaks is determined. That determined isotope ratio is compared to the predetermined ratio of the isotopes present in the molecules of the standard compound prior to the mass spectral analysis. A so determined isotopic ratio being within experimental error of the predetermined ratio indicates that the results of the chromatographic separation were correct. Contrarily, a determined isotopic ratio being greater than experimental error of the predetermined ratio indicates that the results of the chromatographic separation were incorrect.

A contemplated method envisages the use and presence of two or more separate standard compounds of different molecular weight in the sample. Those two or more standard compounds can contain the same or different first and second isotope pairs. When two or more of the same isotope pairs are utilized, the predetermined ratios of isotopes can be the same or different.

The standard compound can be admixed with the sample for mass spectral analysis before of after the sample is chromatographically separated. It is preferred, however, that the standard be admixed with the chromatically separated sample after completion of the chromatographic separation.

In another (non-biological) embodiment of this method, a compound that has a chlorine, oxygen, bromine (or any other element having two stable isotopes) is used. The method requires that the compound be made individually from selected isotopes of chlorine, for example, and then the isotopic distribution of the standard adjusted for optimal identification.

Illustratively, for an example, chlorine has two major isotopes that are Cl-35 (75% natural abundance) and Cl-37 (24% natural abundance). If the molecule that is used as a standard has only one chlorine, one can obtain a molecule that will appear in the spectrum in at both it base mass; i.e. that with the Cl-35, and an M+2 with an equal height by the incorporation of an equal mixture of the two chlorine isotopes in the molecule (see FIGS. 1 and 2), rather than using the natural abundances. A molecule that has a single chlorine atom within the molecule can be used this way in order to find molecules that are chemically stable and have a wide range of chemical characteristics. If one uses a molecule that has two or more chlorines, the patterns that can be achieved are quite complex; i.e., with two chlorines there are three peaks. In other manifestations, other elements with suitable stable isotopic distributions can be employed in a similar manner; these may include oxygen (O-16 and O-18), bromine (Br-79 and Br-81).

Benefits from this aspect of the invention include: a) it is unlikely that any single contaminating molecule will render the standard unusable, and b) the predetermined isotopic pattern that is built into the standard is easily identifiable by a person or software. Each of these benefits is discussed below.

In the current use of standards, the material employed is generally similar to the analyte that is being measured and yet is differentiable in some manner. This often means that a simple replacement of an isotope of the analyte can be replaced. For instance, one could replace any hydrogen in an analyte molecule and use the molecule as a standard for the analyte. In reality, however, such a standard would be flawed as the mass of the standard will fall largely within the normal isotopic distribution of analyte, and thus in more realistic situations more that one atom will be replaced in order to get out from under the "normal" isotopic shadow of an analyte. Even when one is able to shift the standard out from an analyte's normal distribution, there is no assurance that there is no other molecule in whose isotopic shadow the standard will fall.

A compound considered here is generally not biologically transformed if it is to be used as a standard. But rather, the isotopic patterns are inherent at the time of their usage.

In these non-biological uses, the isotopic patterns assist in aiding and strengthening the ability and ease of a user to identify them. Once they are identified in a mixture the isotopic patterns provide multiple peaks, any one of which can be used for quantification. Thus, if it is the case that neither isotopic peak is interfered with by a contaminating compound, either peak can reliably be used for quantification. However, if the isotopic peaks do not demonstrate the appropriate ratios, it can be understood that the outlier is the one that has an abnormally large size and the true quantification can be calculated from the others. Thus, this technique permits one to remove the offending contamination and achieve a more accurate estimation of the true quantity of the compound in question.

Another aspect of the invention contemplates the use of two or more standards. Here, each of the molecules of the first standard compound contains one or the other of a pair of two stable isotopes of the same element that differ in molecular weight by at least two atomic mass units. Those two isotopes are present in the molecules of the first standard compound in a predetermined ratio that is other than the naturally occurring ratio of those isotopes, as was discussed previously.

The second standard compound also contains one or the other of a second pair of two stable isotopes of the same element that differ in molecular weight by at least two atomic mass units. These two isotopes are present in the molecules of the second standard compound in a predetermined ratio that is also other than the naturally occurring ratio of those isotopes. The molecular weights of the first standard compounds are different from the molecular weights of said second standard compound. For example, the first standard compound could be 2-chloro-2-deoxyglucose, whereas the second standard is 2-chloro-2-deoxyroribose.

Thus, in one aspect, the first and second isotope pairs are the same. In another aspect, the first and second isotope pairs are the different. Here, for example, one could use 2-chloro-2-deoxyribose and 2-bromo-2-glucose. Alternatively, one could use 2-chloro-2-deoxyglucose and 2-bromo-2-deoxyglucose. The pairs of stable isotopes are again preferably Cl-35 and Cl-37, or O-16 and O-18, or Br-79 and Br-81, or a mixture of two or three of those isotope pairs.

The components of a typical sample to be mass spectrally analyzed are themselves typically separated prior to introduction into the mass spectrometer. That separation can be carried out using gas chromatography, high pressure liquid chromatography (HPLC), size exclusion chromatography, electrophoresis and the like. Various separation techniques can also be combined.

Illustrative equipment that can be used to carry out a contemplated method include the following.

Mass Spectrometers:

Agilent 6520 Accurate-Mass Q-TOF LC/MS, Agilent 5975 Series MSD, Thermo-Fisher LTQ, Thermo-Fisher ORBITRAP®, Waters MICROMASS® GCT Premier™, and Waters LCT Premier™.

Separation systems can be part of the MS (as in GC) or separate, and illustratively include: Waters ACQUITY UPLC®, Agilent Rapid Resolution, and Thermo Surveyor Plus systems.

As is well known in the art, analysis of the mass spectra is typically accomplished with the aid of so-called "peak-picker" software that is designed to identify and report mass spectral ion peaks. This software is available commercially, in open access, and from private workers. One such program is disclosed in Katajamaa et al., BMC *Bioinformatics* 2005, 6:179; doi:10.1186/1471-2105-6-179, whereas another is disclosed in Rögnvaldsson et al., 2004 *J. Chrom. B*, 807(2): 209-215; doi:10.1016/j.jchromb.2004.04.010. Commercial products are illustrated by those available under the name RAZOR TOOLS/6™ from Spectrum Square Associates, 755 Snyder Hill, Ithaca N.Y. 14850 USA.

A contemplated method is general in its applicability, and is illustrated by the following specific examples.

EXAMPLE 1

Internal Standard

This method uses the abnormal isotopic distribution (rather than enriched) of a compound to identify that compound as a specific standard when it is inserted into a mixture of other compounds which will not show the same form of abnormality. This method requires only that the molecules be synthesized with purified isotopes of chlorine, oxygen, or bromine (or other elements with distinctive isotopic distributions) and then mixed to achieve the desired isotopic ratio and used as standards where their distinctive non-naturally occurring isotopic distribution patterns become the identifier for the standard. Alternatively, the elemental isotopic composition can be achieved prior to the final synthetic step whereby the resulting synthetic products possess the desired isotopic signature.

The ideal abnormal pattern can be as simple as a one-to-one ratio of the parent ion and its associated M+2 (see FIG. 2), or more complex as the need arises. The key element is that the isotopic signature be unique and easily identifiable even in the presence of a co-eluting molecule with which it can share an atomic mass.

Thus, as one prepares a sample of any description for analysis, one can add to it a wide variety of chemicals each one of which has a unique isotopic signature. Because the isotopic signature cannot be achieved in any natural substance, each of these standards can be uniquely identified after the analysis. When it is identified, either its presence or amount (quantity) can be the characteristic that is sought.

If the compound were used as a measure of a process, its quantity is likely the significant feature. Thus, if a compound were used as a recovery standard, derivatization standard, injection standard or process standard, the quantity that is inserted before quantitation is carefully controlled and the quantity seen after quantitation is indicative of the success of all intervening processes.

In some cases, the standard can be inserted in the very last step, in these situations the standard's presence can be more important than its quantity, as the critical value measured is the response during the analysis.

In each of these cases, if the compound used as a standard does not have a unique characteristic, its value can be compromised by another compound that has an overlapping feature. Where the compounds used as standards contain unique isotopic distributions that can not be attained in the natural world, there is less likelihood of such a misidentification.

In the simplest case, if the molecule has been constructed with a 50:50 mixture of chlorine, oxygen, or bromine isotopes, the compound will exhibit two mass spectral peaks that are separated by two mass units. Such a compound will be unlikely to be missed or interfered with because if any natural compound interferes with one of the two peaks, the other will so indicate and permit one to ignore the false data.

Each of the patents and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

What is claimed:

1. A composition adapted for mass spectral analysis comprised of a mass spectrally-determinable amount of each of (i) at least one analyte to be assayed and (ii) a standard compound, each of the molecules of the standard compound contains one or the other of a pair of two stable isotopes of the same element that differ in molecular weight by at least two atomic mass units, said two isotopes being present in the molecules of said standard compound in a predetermined ratio that is other than the naturally occurring ratio of those isotopes.

2. The composition according to claim 1, wherein the pair of stable isotopes is Cl-35 and Cl-37, or O-16 and O-18, or Br-79 and Br-81, or a mixture of two or three of those isotope pairs.

3. The composition according to claim 1, wherein said at least one analyte to be assayed has a molecular weight of about 15,000 amu or less.

4. The composition according to claim 3, wherein said at least one analyte to be assayed has a molecular weight of about 5,000 amu or less.

5. The composition according to claim 4, wherein said at least one analyte to be assayed has a molecular weight of about 1,000 amu or less.

6. The composition according to claim 1, wherein said composition contains a plurality of analytes to be assayed.

7. The composition according to claim 1, wherein said composition contains two standard compounds,
wherein each of the molecules of the first standard compound contains one or the other of a pair of two stable isotopes of the same element that differ in molecular weight by at least two atomic mass units, said two isotopes being present in the molecules of said first standard compound in a predetermined ratio that is other than the naturally occurring ratio of those isotopes, and
wherein said second standard compound contains one or the other of a second pair of two stable isotopes of the same element that differ in molecular weight by at least two atomic mass units, said two isotopes being present in the molecules of said second standard compound in a predetermined ratio that is other than the naturally occurring ratio of those isotopes, the molecular weights of the first standard compounds being different from the molecular weights of said second standard compound.

8. A method for determining the presence of a standard within a complex mass spectrographic assay of a sample that comprises the steps of:
a) providing a sample for analysis that comprises a composition adapted for mass spectral analysis that contains a mass spectrally-determinable amount of each of (i) at least one analyte to be assayed and (ii) a standard compound, wherein each of the molecules of the standard compound contains one or the other of a pair of two stable isotopes of the same element that differ in molecular weight by at least two atomic mass units, said two isotopes being present in the molecules of said standard compound in a predetermined ratio that is other than the naturally occurring ratio of those isotopes;
b) carrying out the mass spectral analysis of the sample to provide a set of analyte ion peaks, including peaks for the ions produced by the standard compound molecules that contain said two isotopes;
c) determining the ratio of said two isotopes to each other;
d) comparing the determined isotope ratio of step c) to the predetermined ratio of said isotopes present in the molecules of the standard compound prior to the mass spectral analysis, wherein an isotopic ratio determined in step c) being within experimental error of the predetermined ratio indicating that the results of the mass spectral analysis of step b) were correct, and an isotopic ratio determined in step c) being greater than experimental error of the predetermined ratio indicating that the results of the mass spectral analysis of step b) were incorrect.

9. The method according to claim 8, wherein the pair of stable isotopes is Cl-35 and Cl-37, or O-16 and O-18, or Br-79 and Br-81, or a mixture of two or three of those isotope pairs.

10. The method according to claim 8, wherein said at least one analyte to be assayed has a molecular weight of about 15,000 amu or less.

11. The method according to claim 10, wherein said at least one analyte to be assayed has a molecular weight of about 5,000 amu or less.

12. The method according to claim 11, wherein said at least one analyte to be assayed has a molecular weight of about 1,000 amu or less.

13. The method according to claim 8, wherein said composition contains a plurality of analytes to be assayed.

14. The method according to claim 8, wherein said composition contains two standard compounds,
wherein each of the molecules of the first standard compound contains one or the other of a pair of two stable isotopes of the same element that differ in molecular weight by at least two atomic mass units, said two isotopes being present in the molecules of said first standard compound in a predetermined ratio that is other than the naturally occurring ratio of those isotopes, and
wherein said second standard compound contains one or the other of a second pair of two stable isotopes of the same element that differ in molecular weight by at least two atomic mass units, said two isotopes being present in the molecules of said second standard compound in a predetermined ratio that is other than the naturally occurring ratio of those isotopes, the molecular weights of the first standard compounds being different from the molecular weights of said second standard compound.

15. The method according to claim 14, wherein said first and second isotope pairs are the same.

16. The method according to claim 14, wherein said first and second isotope pairs are the different.

17. The method according to claim 14, wherein the pairs of stable isotopes are Cl-35 and Cl-37, or O-16 and O-18, or Br-79 and Br-81, or a mixture of two or three of those isotope pairs.

18. A method for determining the correctness of a chromatographic separation of a sample that comprises the steps of:
a) providing a chromatographically separated sample for analysis that comprises a composition adapted for mass spectral analysis that contains a mass spectrally-determinable amount of each of (i) at least one analyte to be assayed and (ii) a standard compound, wherein each of the molecules of said standard compound contains one or the other of a pair of two stable isotopes of the same element that differ in molecular weight by at least two atomic mass units, said two isotopes being present in the molecules of said standard compound in a predetermined ratio that is other than the naturally occurring ratio of those isotopes;
b) carrying out the mass spectral analysis of the sample to provide a set of analyte ion peaks, including peaks for the ions produced by the standard compound molecules that contain said two isotopes;
c) determining the ratio of said two isotopes to each other in the standard compound peaks;
d) comparing the determined isotope ratio of step c) to the predetermined ratio of said isotopes present in the molecules of the standard compound prior to the mass spectral analysis, wherein an isotopic ratio determined in step c) being within experimental error of the predetermined ratio indicates that the results of the chromatographic separation were correct, and an isotopic ratio determined in step c) being greater than experimental error of the predetermined ratio indicates that the results of the chromatographic separation were incorrect.

19. The method according to claim 18, wherein two separate standard compounds are present.

20. The method according to claim 19, wherein the two standard compounds contain two different first and second isotope pairs.

21. The method according to claim 18, wherein said standard is admixed with the chromatically separated sample after completion of the chromatographic separation.

* * * * *